United States Patent
Kocks et al.

(10) Patent No.: US 10,099,319 B2
(45) Date of Patent: Oct. 16, 2018

(54) DEVICE FOR CONNECTING THE ENDS OF PIPES MADE OF STEEL BY MEANS OF AN ORBITAL WELDING PROCESS

(71) Applicant: SALZGITTER MANNESMANN LINE PIPE GMBH, Siegen (DE)

(72) Inventors: Hans-Jürgen Kocks, Freudenberg (DE); Jörn Winkels, Werl (DE); Steffen Keitel, Halle (DE); Jan Neubert, Leipzig (DE); Sebastian Rude, Bad Dürrenberg (DE)

(73) Assignee: Salzgitter Mannesmann Line Pipe GmbH, Siegen (DE)

( * ) Notice: Subject to any disclaimer, the term of this patent is extended or adjusted under 35 U.S.C. 154(b) by 209 days.

(21) Appl. No.: 14/391,609

(22) PCT Filed: Mar. 26, 2013

(86) PCT No.: PCT/DE2013/000179
§ 371 (c)(1),
(2) Date: Oct. 9, 2014

(87) PCT Pub. No.: WO2013/152752
PCT Pub. Date: Oct. 17, 2013

(65) Prior Publication Data
US 2015/0060436 A1    Mar. 5, 2015

(30) Foreign Application Priority Data

Apr. 10, 2012   (DE) .................. 10 2012 007 563

(51) Int. Cl.
*B23K 9/028*    (2006.01)
*B23K 31/12*    (2006.01)
(Continued)

(52) U.S. Cl.
CPC .......... *B23K 31/125* (2013.01); *B23K 9/0286* (2013.01); *B23K 9/1274* (2013.01);
(Continued)

(58) Field of Classification Search
CPC . B23K 9/02; B23K 9/12; B23K 9/028; B23K 9/0282; B23K 9/0286; B23K 9/0288
(Continued)

(56) References Cited

U.S. PATENT DOCUMENTS 3,207,881 A * 9/1965 Pagan .................. B23K 9/0286
219/60 A
3,306,116 A * 2/1967 Ross .................... B23K 9/0286
219/125.12
(Continued)

FOREIGN PATENT DOCUMENTS

AU           65060 74         7/1975
DE           103 34 446       2/2005
(Continued)

OTHER PUBLICATIONS

International Search Report issued by the European Patent Office in International Application PCT/DE2013/000179.

*Primary Examiner* — Dana Ross
*Assistant Examiner* — Ayub Maye
(74) *Attorney, Agent, or Firm* — Henry M. Feiereisen LLC

(57) ABSTRACT

A device for connecting the ends of pipes, which are aligned, tack-welded and made of steel, by an orbital welding process using a welding joint formed by the pipe ends and using tools which can be orbitally moved about the welding joint for welding and checking the seam. The device includes guide base plates placed on both sides at each pipe end in the region of the welding joint and rigidly clamped to the pipe ends. The guide base plates centrally have a circular recess
(Continued)

Figure 1:
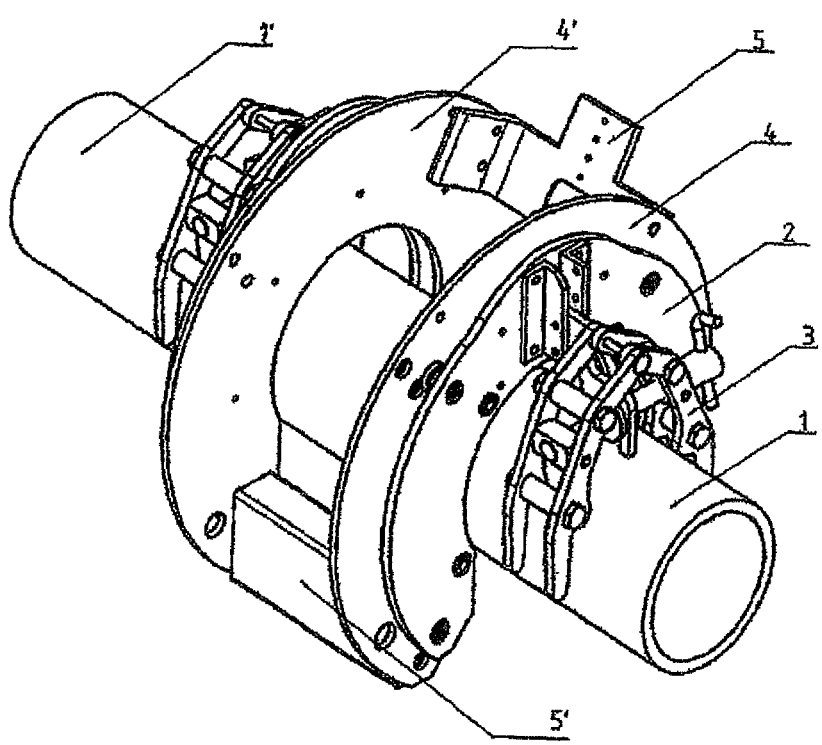

with a radial opening for the feed-through of the pipes to be welded. The guide base plates include clamping elements rigidly connected to each guide base plate face facing away from the welding joint, and a frame for receiving the welding and checking tools, the frame rotatably mounted between the guide base plates and centrally pivotal about the pipe ends by at least 360°.

11 Claims, 2 Drawing Sheets

(51) Int. Cl.
*B23K 31/02* (2006.01)
*B23K 9/127* (2006.01)
*B23K 9/23* (2006.01)
*B23K 26/10* (2006.01)
*B23K 26/14* (2014.01)
*G01N 29/265* (2006.01)
*B23K 26/282* (2014.01)
*B23K 101/06* (2006.01)
*B23K 103/04* (2006.01)

(52) U.S. Cl.
CPC .............. *B23K 9/23* (2013.01); *B23K 26/103* (2013.01); *B23K 26/1429* (2013.01); *B23K 26/282* (2015.10); *B23K 31/027* (2013.01); *G01N 29/265* (2013.01); *B23K 2201/06* (2013.01); *B23K 2203/04* (2013.01); *G01N 2291/0289* (2013.01); *G01N 2291/267* (2013.01)

(58) Field of Classification Search
USPC ...................... 219/59.1, 60 A, 60 R
See application file for complete search history.

(56) References Cited

U.S. PATENT DOCUMENTS

| | | | |
|---|---|---|---|
| 3,668,359 A | 6/1972 | Emmerson | |
| 4,051,342 A | 9/1977 | Stubbings | |
| 4,243,868 A * | 1/1981 | Graham | B23K 9/0286 219/125.11 |
| 4,330,074 A * | 5/1982 | Minkiewicz | B23K 9/0286 228/29 |
| 4,527,033 A * | 7/1985 | Matsuyama | B23K 9/0253 219/60 R |
| 4,577,796 A * | 3/1986 | Powers | B23K 9/1274 228/102 |
| 4,804,813 A * | 2/1989 | Tesch | B23K 9/0286 219/59.1 |
| 6,887,020 B2 | 5/2005 | Winkels | |
| 7,012,217 B2 | 3/2006 | Titze | |
| 8,373,083 B2 | 2/2013 | Neubert | |
| 2004/0191023 A1 | 9/2004 | Winkels | |
| 2005/0035094 A1 | 2/2005 | Titze | |
| 2007/0210047 A1* | 9/2007 | Child | B23K 9/1274 219/124.34 |
| 2010/0206850 A1 | 8/2010 | Neubert | |
| 2013/0063590 A1 | 3/2013 | Deppe | |

FOREIGN PATENT DOCUMENTS

| | | |
|---|---|---|
| GB | 2 195 570 | 4/1988 |
| WO | 2005-056230 | 6/2005 |

* cited by examiner

US 10,099,319 B2

DEVICE FOR CONNECTING THE ENDS OF PIPES MADE OF STEEL BY MEANS OF AN ORBITAL WELDING PROCESS

CROSS-REFERENCES TO RELATED APPLICATIONS

This application is the U.S. National Stage of International. Application No. PCT/DE2013/000179, filed Mar. 26, 2013, which designated the United States and has been published as International Publication No. WO 2013/152752 and which claims the priority of German Patent Application, Serial No. 10 2012 007 563.4, filed Apr. 10, 2012, pursuant to 35 U.S.C. 119(a)-(d).

BACKGROUND OF THE INVENTION

The invention relates to a device for connecting the ends of steel pipes by means of orbital welding.

In particular, the invention relates to the welding of pipes, which may for example have wall thicknesses of 2 to 20 mm and a diameter of 60 to 1600 mm and which are connected to each other to form pipe lines by means of different welding procedures such as laser beam welding, combined laser beam/laser arc welding or electric arc welding. In the following, pipes are understood as circular pipes as well as hollow profiles with different cross sections.

The orbital welding of pipes is generally known for example from DE 103 34 446 A1. Here an orbital welding device for connecting two pipe ends is disclosed, wherein the device is attached and clamped to a first pipe end and the second pipe end is brought into welding position in so as to confront the first pipe end. By means of two welding heads which are offset relative to each other by 180° and which are guided pivotal about an axis, a 360° circular welding seam can be achieved. A disadvantage is that two welding heads are required in order to weld the pipe along the entire circumference.

A further orbital welding device is known from WO 2005/0-56230 A1 in which a combination of metal protective gas welding and laser arc welding is used. This so called laser MSG hybrid welding is characterized in that the electric arc and the laser beam are arranged at a defined distance to ach other and a higher gap bridging capacity can be achieved compared to a pure laser beam welding process. The device includes a guide ring, which can be oriented relative to the end of the first pipe. The orientation occurs via multiple clamping screws, which are arranged along the guide ring circumference and by means of which the distance of the guide ring to the pipe surface can be adjusted. The guide ring serves for guiding an orbital carriage, which can be moved thereon and which can accommodate further components for process monitoring and welding seam checking. The described device is used in mobile application for orbital welding of pipes to pipelines.

A disadvantage of this device is the complex construction with guide rings that are closed about the pipe and the elaborate alignment and centering of the pipe ends. Especially the centering requires great effort in the case of large pipe diameters and requires additional centering devices in the device having correspondingly great holding forces in order to ensure a geometrically stable welding groove during the welding. This makes the device very heavy and it can its use in mobile application is very difficult.

In addition the sequence of the welding process is very complex in which the pipe ends have to be inserted into the device and centered and subsequently the welded pipe has to be moved lengthwise out of the device.

In summary, no industrially applicable orbital guiding system exists in the state of the art that is optimally adjusted to the demands regarding quality and economical efficiency of the orbital welding.

SUMMARY OF THE INVENTION

It is an object of the invention to set forth a device for connecting the ends of steel pipes by means of orbital welding, which overcomes the described disadvantages, i.e., which can be cost-effectively produced and flexibly used with small time investment.

This object is solved by a device for connecting ends of aligned and tack-welded pipes by means of orbital welding, including guide base plates each having a central circular recess and a radial opening for centrally receiving pipes to be welded to each other in the circular recess through the radial opening; clamping elements for clamping the guide base plates to the ends of the aligned and tack seam welded pipes, said clamping elements being fixedly connected to respective sides of the guide base plates which face away from a welding joint formed by the ends of the pipes; and a frame with welding tools and testing tools for testing a welding seam received thereon, the frame being arranged between the guide base plates and pivotally supported on respective inner sides of the guide base plates facing the welding joint, so as to be centrically pivotal about the ends of the pipes by at least 360° and to enable orbital movement of the welding tools and testing tools about the welding joint. Advantageous refinements are the subject matter of dependent claims.

The teaching of the invention includes a device for connecting the ends of pipes, in particular steel pipes, by means of orbital welding, which have already been oriented and tack seam welded, with a welding groove which is formed by the ends of the pipes and tools which can be orbitally moved about the welding groove for welding and testing the welding seam, the device being characterized in that it includes guide base plates which can be attached and securely clamped onto the pipe ends on both sides on the respective pipe ends in the region of the welding site, wherein the guide base plates have a central circular recess with a radial opening for centered reception of the pipes to be welded in the recess, with clamping elements which are fixedly connected on the respective side of the guide base plates, which sides face away from the welding groove, for clamping the guide base plates with the pipe ends, and with a frame for receiving the welding and testing tools, which frame is arranged so as to be pivotally supported between the guide base plates on the inner sides and is centrally pivotal about the pipe ends by at least 360°.

For welding, the device is simply placed on the pipe ends with a radial distance to the pipe ends and with the guide base plates symmetrical to the welding groove, and clamped with the pipe ends using the clamping elements which are securely connected with the guide base plates. For this, the diameter of the circular recess in the guide base plates is greater than the diameter of the pipe ends to be received. Advantageously this also enables using the device also for welding of different pipe diameters. The pipe to be welded is located in the circular recess of the guide base plates, wherein the radial distance between guide base plate and pipe is adjusted so that the pivot frame, which is pivotally arranged between the guide base plates with tool holders for welding and testing tools, extends centrally about the longitudinal axis of the pipe to be welded.

The device according to the invention overcomes the disadvantages of the known orbital welding devices on one hand by a very simple and with this cost-effective construction, and on the other hand also in that this device is used advantageously for already aligned, i.e., centered and tack seam welded pipes.

Decoupling the centering and the tack welding of the pipe ends from the actual orbital final welding significantly simplifies the construction of the device and renders it more flexible, i.e., better suited for mobile applications.

With the proposed device the circumferential seam can further be welded over 360° with only one welding head.

Advantageously laser beam welding is used for the joining of the pipes. For this a raw beam generated by a laser beam source is conducted via an optical fiber to an optic fastened on the carriage. This optic forms the laser beam and conducts the laser beam onto the joint of the two pipes. Advantageously an angled optic is used for this purpose, wherein the collimation of the laser beam is 150 mm and the focusing 200 mm. Further an additional so called LWM sensor (Laser Welding-Monitor) is arranged on the optic, which serves for detecting the following parameters:
  emitted plasma glow
  back-reflected laser radiation
  reflected laser power on the beam splitter The reason for using an angled optic is to reduce the work area required by the optical fiber. The optical fiber has a large bending radius and would strongly increase the required work area for the circumferential movement. By using an angled optic the optical fiber can be installed and connected in the direction of the longitudinal axis of the pipe. The feed movement of the optic occurs via two feed axes, which for an accurate positioning of the process in Y-direction (longitudinal relative to the pipe axis) and Z-direction (in radial direction relative to the pipe surface) are advantageously constructed as ball screw transmission.

For detecting a welding joint, in particular an edge offset and gap, an advantageous refinement of the invention provides for detecting the line generated by a line laser transverse to the joint by a camera. The thus detected values are used for the seam programming. The laser line is detected by a camera software and influences via a position calculation the vertical and lateral adjustment of the optic. Subsequent to the welding process the camera is used for determining a topography of the seam. Like the optic the camera and the linear laser are arranged centrally between the two pivot brackets on the carriage and are guided about the pipe with the circumferential movement.

For determining inner welding defects two ultrasound testing probes are guided about the pipe so as to trail the welding head. One of each of the welding heads is arranged on either side of the welding seam. The testing probes themselves are arranged pivotal as cylinders and advantageously function without requiring coupling means. They are arranged at a distance to the joint which distance can be adjusted via axes, and are kept in contact with the pipe via spring tension. For different pipe diameters however a height adjustment is also possible via axes. Like the optic and camera the ultrasound testing probes are also arranged centrally between the two inner plates and are moved together with the inner plates about the pipe.

The device is operated via an external control via which the laser system and the hardware can be controlled. It also detects and analyzes all data of the camera of the ultrasound testing probes and the LWM sensor situated on the optic. A software is used to determine and initiate the exact program sequence.

In addition to the tools required for the actual welding process further tools or components required for the welding process, for supporting the welding process or for subsequent manufacturing steps can be guided by means of the carriage. This can for example be a seam tracking system or measuring means for destruction-free quality control of the welding seam by way of seam measurement or defect detection. By means of a system, which is moved ahead of the welding process, the welding groove can be detected and the subsequent welding process can be adjusted in its position.

By means of for example optical systems a quality control of the welding seam is also possible.

DETAILED DESCRIPTION OF PREFERRED EMBODIMENTS

FIG. 1 illustrates the basic construction of the device according to the invention. It includes the two circular guide base plates 2, which are provided with a radial opening in order to be able to attach them onto the pipes 1, 1' to be joined. The inner circular ring diameter is greater than the diameter of the pipes 1, 1' to be welded in order to be able to perform an accurate alignment via the radial clearance for a centric circumferential movement of the welding and testing tools. For fastening the device on the ends of the pipes 1, 1' clamping elements 3 are arranged on the outer welding groove-averted sides of the guide base plates 2, and are used to clamp the two guide base plates 2 with a respective pipe end via clamping elements 3.

A circular ring-shaped pivot bracket 4, 4', which is also provided with a radial opening, is pivotally guided on each of the inner welding groove-facing sides of the guide base plates 2, so that the pivot brackets can also perform a circular movement along the guide base plates 2 about the pipes 1, 1'. The pivot brackets 4, 4' are rigidly interconnected to form a pivot frame via tool holders 5, 5', wherein all components for joining and testing are mounted on the tool holders 5, 5'.

Figure 2:
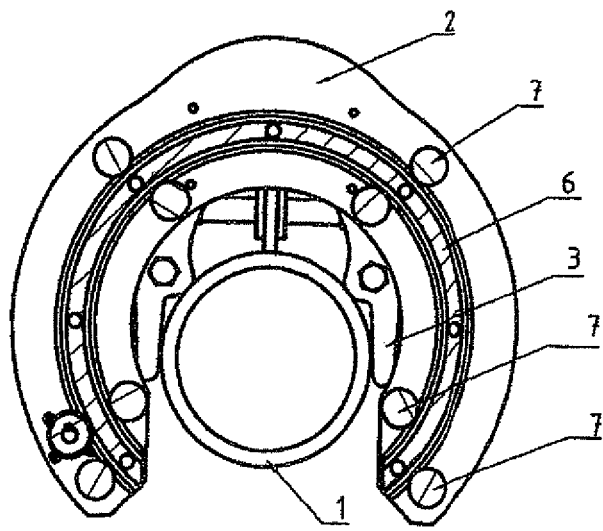

FIG. 2 shows a schematic sectional view of the ring guide of the pivot brackets or the pivot frame. The circular ring-shaped guide base plate 2 is attached to and clamped on the pipe 1 with the aid of the clamping elements 3. Via the radial clearance between the outer diameter of the pipe 1 and the inner diameter of the guide base plate 2 the device can be exactly centrically aligned relative to the longitudinal axis of the pipe 1. In order to enable a circular movement of the pivot brackets 4, 4', the pivot brackets are advantageously guided orbitally pivotal via a circular guide rail 6 arranged respectively between the guide base plates 2 and pivot brackets 4, 4'. The guide rails 6 are arranged on the pivot brackets and are each guided via guide rollers 7, which are arranged on the outer and inner surface of the guide rails 6, and are themselves connected with the guide base plates 2.

For driving the circumferential movement of the pivot frame, a sprocket and a drive motor (here not shown) are arranged according to the invention on both sides respectively between pivot bracket 4, 4' and guide base plate 2. The two sprockets are fastened on the pivot brackets 4, 4' and also perform the circumferential movement. The motors are connected with the guide base plates 2 and transmit the rotational movement via pinions to the sprockets.

In an advantageous refinement of the invention, a transmission consisting of a planetary gear system and a worm gear is arranged between the motor and the pinion. The transmission enables a continuous starting and ending of the rotational movement.

Figure 3:
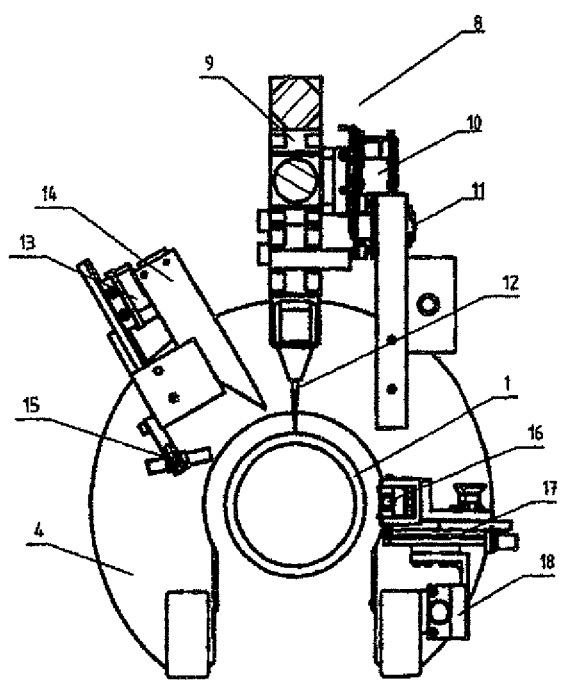

FIG. 3 shows a schematic view of the device attached to the pipe ends taken along the longitudinal axis of the pipe with mounted welding and testing tools on the tool holders 5, 5' arranged between the pivot brackets 4, 4'. For reasons of clarity only the rear pivot bracket 4 and the welding and testing tools, which are fastened thereon via the here not shown tool holders 5, 5', are shown in this view, On the pivot bracket 4 a laser welding device 8 is arranged which can be displaced along different axes, and which includes a welding head 9 and actuating devices for radial height adjustment 10 and for positioning in longitudinal pipe direction 11, with which actuating devices the laser beam 12 can be exactly aligned relative to the welding groove of the pipes 1, 1' to be interconnected.

For programming the required seam geometry and with this for controlling the laser (for example positioning, power), the geometry of the welding joint, in particular edge offset and gap, is detected by a camera 14 by means of a line (here not shown) generated by means of a line laser transverse to the welding groove.

The thus detected parameters are used for the seam programming. The laser line is detected by a camera software and influences via a position calculation the height and lateral adjustment of the optic of the welding head 9. Line laser 13 and camera 14 are provided with an actuating device 15 for height and angle adjustment.

For determining errors in the welding seam directly after the welding, two ultrasound testing heads 16 are arranged on a further here not shown tool holder so that they test the welding seam from both sides. The ultrasound testing probes 16 are arranged pivotal and can be radially adjusted by means of further actuating devices 17, 18 in height and along the longitudinal direction of the pipe relative to the welding seam to be tested. The ultrasound testing probes 16 are preferably suited for testing without requiring coupling means.

The invention claimed is:

1. A device for connecting ends of pipes by means of orbital welding; comprising:
    an external control having a software for operating the device;
    guide base plates each having a central circular recess and a radial opening for centrally receiving the pipes to be welded to each other in the central circular recess through the radial opening, the guide base plates only partially surrounding the pipes to be welded;
    clamping elements for clamping the guide base plates to the ends of the pipes which are aligned and tack seam welded, each said clamping elements being fixedly clamped to each of the pipes by partially surrounding each pipe and fixedly connected to respective sides of the guide base plates which face away from a welding joint formed by the ends of the pipes; and
    a frame, welding tools and testing tools for testing a welding seam arranged on the frame, said frame being arranged between the guide base plates and pivotally supported on respective inner sides of the guide base plates facing the welding joint, so as to be centrically pivotal about the ends of the pipes by at 360° and to enable orbital movement of the welding tools and the testing tools about the welding joint.

2. The device of claim 1, wherein the pipes are made of steel.

3. The device of claim 1, wherein the frame comprises pivot brackets and tool holders for receiving the welding tools and the testing tools, said tool holders connecting the pivot brackets.

4. The device of claim 1, wherein the testing tools comprise a system for destruction free welding seam testing.

5. The device of claim 3, further comprising a circular guide rail arranged between the respective guide base plates and the pivot brackets, said pivot brackets being supported on the circular guide rails for orbital pivoting about the pipes.

6. The device of claim 3, further comprising at least one of laser welding heads, protective gas welding heads and hybrid welding heads mounted on the tool holders.

7. The device of claim 4, wherein the system for destruction free welding seam testing is constructed as an ultrasound testing device.

8. The device of claim 3, further comprising further tools arranged on the tool holders.

9. The device of claim 5, wherein the pivot brackets are supported on the circular guide rails via guide rollers.

10. The device of claim 7, wherein the ultrasound testing device includes at least two ultrasound testing probes which are attachable on the ends of the pipes on both sides of a welding seam formed between the ends of the pipes.

11. The device of claim 8, wherein the further tools include one or more additional welding heads, a seam geometry detection system and/or a seam tracking system.

* * * * *